(12) United States Patent
Frid et al.

(10) Patent No.: US 10,076,434 B2
(45) Date of Patent: Sep. 18, 2018

(54) STENT DELIVERY SYSTEM

(71) Applicant: CARDIATIS S.A., Isnes (BE)

(72) Inventors: Noureddine Frid, Beersel (BE);
Nathalie Simao, La Tessouale (FR);
Aurélie Masquelier, Marbaix-la-Tour (BE); Laurence Gebhart, Brussels (BE)

(73) Assignee: Cardiatis S.A., Isnes (BE)

( * ) Notice: Subject to any disclaimer, the term of this patent is extended or adjusted under 35 U.S.C. 154(b) by 273 days.

(21) Appl. No.: 14/897,868

(22) PCT Filed: Jun. 13, 2014

(86) PCT No.: PCT/EP2014/062455
§ 371 (c)(1),
(2) Date: Dec. 11, 2015

(87) PCT Pub. No.: WO2014/198941
PCT Pub. Date: Dec. 18, 2014

(65) Prior Publication Data
US 2016/0113795 A1    Apr. 28, 2016

(30) Foreign Application Priority Data

Jun. 13, 2013  (EP) .................................... 13171841

(51) Int. Cl.
*A61F 2/06*   (2013.01)
*A61F 2/966*  (2013.01)
(Continued)

(52) U.S. Cl.
CPC ................ *A61F 2/966* (2013.01); *A61F 2/92* (2013.01); *A61F 2002/9534* (2013.01); *A61F 2002/9665* (2013.01)

(58) Field of Classification Search
CPC ...... A61F 2/06; A61F 2/90; A61F 2/95; A61F 2/92; A61F 2/966; A61F 2002/9534; A61F 2002/9665; A61M 25/00; A61B 17/00
See application file for complete search history.

(56) References Cited

U.S. PATENT DOCUMENTS 5,919,204 A  *  7/1999 Lukic ...................... A61F 2/966
                                           606/198
7,588,597 B2      9/2009 Frid
(Continued)

FOREIGN PATENT DOCUMENTS

| EP | 0696447 A2 | 2/1996 |
| EP | 0775470 A1 | 5/1997 |
| WO | WO 2011/014814 A2 | 2/2011 |

*Primary Examiner* — Victor Nguyen
(74) *Attorney, Agent, or Firm* — Leydig, Voit & Mayer, Ltd.; Gerald T. Gray (57) ABSTRACT

An intraluminal apparatus for delivering a self-expanding stent which extends along a longitudinal axis from a proximal side to a distal side. It comprises in delivery configuration (a) a retracting sheath having a lumen along its longitudinal axis and slidably covering a stent receiving region at the distal end of the lumen,
(b) an inner shaft longitudinally disposed in the intraluminal apparatus, at least a distal portion of the inner shaft being disposed within the sheath, (c) the self-expanding stent in a compressed state disposed within the stent receiving region of the lumen, (d) a holding means delimitating an inner cavity, disposed adjacent to a proximal side of the stent in the sheath, the proximal end of the holding means being permanently joined to the inner shaft, and (e) a handling means placed towards the proximal side of the intraluminal apparatus, able to displace longitudinally the retracting sheath with respect to the inner shaft.
When the intraluminal apparatus is in a delivery configuration, the distal portion of the holding means is disposed
(Continued)

around the proximal portion of the stent and defines an overlapping region of the holding means and the stent. The ratio $L_{(10)}/L_{(2)Comp}$ of the length of the overlapping region, $L_{(10)}$, to the length of the self-expanding stent, $L_{(2)Comp}$, in their compressed state is at least 5% and at most 30%.

14 Claims, 11 Drawing Sheets

(51) Int. Cl.
*A61F 2/95* (2013.01)
*A61F 2/92* (2013.01)

(56) References Cited

U.S. PATENT DOCUMENTS

| | | |
|---|---|---|
| 8,048,139 B2 | 11/2011 | Frid et al. |
| 2004/0204749 A1 | 10/2004 | Gunderson |
| 2006/0030923 A1 | 2/2006 | Gunderson |
| 2007/0270932 A1 | 11/2007 | Headley et al. |
| 2011/0082464 A1 | 4/2011 | Douk et al. |

* cited by examiner

STENT DELIVERY SYSTEM

CROSS-REFERENCE TO RELATED APPLICATIONS

This application is a U.S. national phase of International Patent Application No. PCT/EP2014/062455, filed Jun. 13, 2014, which claims the benefit of European Patent Application No. 13171841.3, filed Jun. 13, 2013, the disclosure of which is incorporated by reference in its entirety.

TECHNICAL FIELD

The present invention relates to medical devices and methods for placement of stents into body lumens permitting possible repositioning these stents during placement. The invention applies particularly to self-expanding stents.

BACKGROUND OF THE INVENTION

Stents, grafts, stent-grafts and similar implantable medical devices, collectively referred to hereinafter as stents, are radially expandable endoprostheses. Stents may be implanted in a variety of body lumens or vessels such as within the vascular system, urinary tracts, bile ducts, etc. Stents are generally tubular devices for insertion into body lumens. Stents are typically delivered via a catheter in an unexpanded configuration to a desired body lumen. Once at the desired location, the stent is deployed and implanted in the body lumen. Typically, a stent will have an unexpanded (closed) diameter for delivery and a deployed (opened) diameter after placement in the body lumen. They may be self-expanding, mechanically expandable or hybrid expandable.

Self-expanding stents are typically implanted in a blood vessel or other body lumen at the site of a stenosis or aneurysm by so-called "minimally invasive techniques" in which the stents are compressed radially inwards and are delivered by a catheter to the site where the stents are required through the patient's skin or by a "cat down" technique in which the blood vessel to be treated is exposed by minor surgical means. Self-expanding stents may be constructed from a variety of materials such as stainless steel, Elgiloy®, nickel, titanium, Nitinol®, Phynox®, shape-memory polymer etc. Stents may also be formed in a variety of manners as well. For example a stent may be formed by etching or cutting the stent pattern from a tube or sheet material; a sheet of metal may be cut or etched according to the desired pattern whereupon the sheet may be rolled or otherwise formed into the desired substantially tubular, bifurcated or other shape of stent; one or more wires or ribbons of stent material may be woven, braided or otherwise formed into a desired shape and pattern. Stents may include components that are welded, bonded or otherwise engaged to one another.

In some systems for the delivering of self-expanding stents, the stent is deployed by a retracting sheath system (i.e., pull-back sheath system). In such technique, the compressed stent is preloaded into a distal portion of a retracting sheath included in the delivery system. The delivery system is driven by an operator from the proximal side on through the vascular system until the distal end of the sheath reaches the implantation site. Then the stent is pushed out from the distal end of the system, and caused or allowed to expand to a predetermined diameter in the vessel. When the stent is constrained within the system, the stent is exerting a force onto the inside diameter (ID) of the sheath. Perceived problems with conventional stent delivery systems include a negative interaction of the sheath with the stent caused by the frictional interface between the stent and sheath which prevents the system from properly deploying the stent.

US 2006/0030923 discloses a stent delivery system comprising a retracting sheath and a roll-back inner membrane having a lubricious coating. The inner membrane is disposed directly around a stent and the sheath is disposed around the membrane. The distal end of the membrane is engaged to a distal portion of the sheath and proximal end of the membrane is engaged to a portion of an inner catheter shaft proximal of a stent retaining region of the delivery system. Since the inner membrane rolls back proximally along the length of the stent until the stent is fully exposed and deployed when the pull-back sheathe is retracted, the frictional interface between the stent and sheath is reduced and thus the stent can be properly deployed. However, since the membrane must cover at least all length of the stent within the delivery system, a total volume of the components included in the system becomes bulky and a diameter of the delivery system has to be greater than a diameter of the system without the membrane. It will reduce flexibility and usability of the delivery system.

Perceived problems also include "stent-jumping" which is longitudinal displacement of a self-expending stent, when a retracting sheath is withdrawn from the stent. It occurs because expansion force of the stent is greater than the stent frictional force and stent constraint force at an angle exiting the system.

US 2004/0204749 discloses a stent delivery system comprising a shaft having a plurality of protrusions extending radially outward from a surface thereof. A proximal portion of a stent loaded into the system is temporarily engaged to the protrusions until the engaged portion of the stent is freed to expand. This engagement prevents the stent from moving longitudinally relative to the system (i.e., stent jumping) by controlling the expansion force of the stent at an angle exiting the system during placement of the stent. In order to increase delivery accuracy, a stent delivery system is desired not only to prevent "stent jumping" but also to comprise a re-sheathing function which allows a partially unsheathed stent to be drawn back into the delivery system for repositioning. The protrusions discloses in US 2004/0204749 is not able to re-sheath the partially unsheathed stent because the protrusions do not provide sufficient holding force to make an efficient re-sheathing movement.

EP0775470 A1 discloses a stent delivery device having a scratch protection means for preventing a vessel from being dangerously scratched and perforated by the edges of stent. In a delivery configuration, the scratch protection means is positioned in the sheath and partially engaged to the proximal end of the stent. Since the scratch protection means is formed by a tube of thermoformable material heat shrunk on the shaft but not of self-expanding property, sufficient holding force to make an efficient re-sheathing movement for accurate deployment cannot be expected.

WO 2011/014814 discloses a stent delivery system comprising a pair of forceps-like holders and a middle bumper disposed on an inner shaft. A stent is pinched between the holders and the middle bumper within an outer sheath of the system by keeping the proximal ends of the holders in a hypotube, which is disposed about the shaft, during placement. At the desired place, the stent can be unsheathed and, if necessary, it can be re-sheathed by sliding back the sheath over the stent until the stent is released from the holders and the middle bumper by retracting the hypotube proximally and putting holders in their open position. Although this system may improve the delivery accuracy by providing the re-sheathing function, via the pair of forceps-like holders and the middle bumper, it has poor flexibility because of the rigid property of the holder and middle bumper required for ensuring a sufficient holding ability. Furthermore, because of the additional component like hypotube for making the pinching action of the holders, the system becomes more bulky (the diameter of the system becomes greater) and less flexible. It fatally reduces the usability of the stent delivery system, especially for tiny vessels.

US2011/0082464 discloses an implant delivery system having a first expandable means for loading a polymeric tubular implant into the system without damage. This first expandable means is attached to the distal end of an inner shaft. The distal end of this first expandable means is designed to be engaged to and surrounding a proximal end of the implant upon loading this implant into the delivery system. Since the first expandable means is for loading, once the implant is loaded into the system, the first expandable means is pulled away and does no longer cover any part of the implant. Therefore, US2011/0082464 discloses neither a delivery configuration including the first expandable means nor any effective overlap ratio of the implant with the first expandable means within an outer sheath for improving deployment accuracy. US2011/0082464 further discloses an enlarged diameter portion positioned on the inner shaft and mentions that its use may be helpful in withdrawing the first expandable member over the implant because it can prevent the implant from being dragged proximally when the first expandable means is withdrawn from the delivery system after the loading of the implant. US2011/0082464, however, fails to disclose a delivery configuration comprising an enlarged diameter portion positioned within the first expandable means.

US2007/0270932 also discloses a system for loading a stent into a delivery system with an engaging member having an open distal end as stent holding means. Again, since this engaging member is designed for loading, US2007/0270932 fails to disclose a solution for obtaining a lower profile of a delivery system while keeping adequate deployment accuracy.

U.S. Pat. No. 8,048,139 discloses a stent delivery system with an expendable braided bumper as stent holding means. The braided bumper is joined to a shaft (i.e., a pusher) disposed within a retracting sheath and a self-expanding stent is disposed around the bumper and the shaft. By using the expansion force exerted by the bumper onto the inner surface of the stent within the retracting sheath, the partially deployed stent can be drawn back. The braided structure occupies only a small diameter when folded up and thus provides flexibility during placement. However, since the system utilizes the expansion force of the bumper in order to hold a proximal portion of the stent, it increases the undesired frictional force between an inner surface of the sheath and an outer surface of stent, resulting in increasing the risk of undesired proximal shifting of stent during the deployment step.

SUMMARY OF THE INVENTION

An object of the invention is to provide a stent delivery apparatus with improved delivery accuracy, particularly comprising a function re-sheathing a partially unsheathed stent into a retracting sheath while keeping high flexibility and usability of the delivery apparatus.

Another object of the invention is to provide such an improved stent delivery apparatus with reduced cumbersomeness, i.e. despite its improved properties, the diameter of this apparatus would remain as close as possible to the diameter of an apparatus according to the present state of the art.

The subject of the present invention is defined in the appended independent claims. Preferred embodiments are defined in the dependent claims.

A subject of the present invention is an intraluminal apparatus for delivering a self-expanding stent. This apparatus is designed to be driven by an operator from the proximal side on through the vascular system or a body lumen so that the distal end of the apparatus can be brought close to the implantation site, where the stent can be unloaded from the distal end of the apparatus.

The apparatus extends along a longitudinal axis from a distal side to a proximal side and comprises, in delivery configuration, (a) a retracting sheath having a lumen along its longitudinal axis and slidably covering a stent receiving region placed at the distal end of the lumen, (b) an inner shaft longitudinally and centrally disposed in the apparatus, at least a distal portion of the inner shaft being disposed within the sheath, (c) the self-expanding stent in a compressed state disposed within the stent receiving region of the lumen, (d) a holding means delimitating an inner cavity, disposed adjacent to a proximal side of the stent in the sheath, the proximal end of the holding means being permanently joined to the inner shaft, and (e) a handling means placed towards the proximal side of the lumen, able to displace longitudinally the retracting sheath with respect to the inner shaft. The holding means has a self-expanding property capable of radially expanding from a compressed state within the apparatus having the delivery configuration to an expanded state. The holding means is formed by braiding or weaving a plurality of filaments made of an elastic material. In the expended state, the diameter of the cavity of the holding means is radially increased toward its distal end.

When the apparatus is in the delivery configuration, the distal portion of the holding means is disposed around the proximal portion of the stent and defines an overlapping region of the holding means and the stent. When the apparatus is in the delivery configuration, the ratio of the length of the overlapping region, $L_{(10)}$, to the length of the self-expanding stent, $L_{(2)Comp}$, in their compressed state, $L_{(10)}/L_{(2)Comp}$, is at least 5% and at most 30%. Advantageously, the ratio, $L_{(10)}/L_{(2)Comp}$, is at least 10% and at most 25%, preferably at least 15%, more preferably at least 20%.

Preferably, the inner shaft further comprises a radial protrusion surrounding one portion of the inner shaft. In the delivery configuration, this radial protrusion is positioned outside and adjacent to the proximal end of the stent in the inner cavity of the holding means so as to assist the inner shaft in pushing the stent toward the distal end of the apparatus.

According to an advantageous embodiment, in the expanded state, the holding means adopts either one of (i) a U-shape, (ii) a truncated cone-shape, or (iii) a truncated cone-shape having a cylindrical portion at the distal end thereof.

According to another advantageous embodiment, the holding means is formed of a multilayer braiding. Preferably, it comprises a distal portion with an angle ($\alpha$) formed between braided filaments being, in expanded state, at least 120°, and preferably at least 150°.

Advantageously, the elastic material of the filaments is shape memory material selected from a group consisting of Nitinol® and cobalt-based alloy such as Elgiloy® and Phynox®.

According to another advantageous embodiment, in their respective expanded state, the diameter of the holding means at its distal end, $\varnothing_{(3)Exp}$, is greater than the diameter of the stent (2), $\varnothing_{(2)Exp}$.

Preferably, the self-expanding stent comprises a meshed structure obtained by braiding, weaving or knitting filaments. Advantageously, the meshed structure is a multilayer braiding.

According to another advantageous embodiment, the apparatus further comprises a membrane disposed within the cavity of the holding means. The proximal end of the membrane permanently joins to the inner shaft adjacent the bottom of the cavity. A distal portion of the membrane is, in delivery configuration, disposed around the proximal portion of the stent.

According to another advantageous embodiment, the retracting sheath and the holding means further comprise a radiopaque material around the distal ends of the sheath and the holding means.

A supplemental sheath such as catheter can be used as an extension of the retracting sheath surrounding the distal end of the apparatus.

BRIEF DESCRIPTION OF THE FIGURES

Other particularities and advantage of the invention will be described hereafter of series of particular embodiments, reference being made to the appended drawings in which.

DETAILED DESCRIPTION OF THE INVENTION

Figure 1:
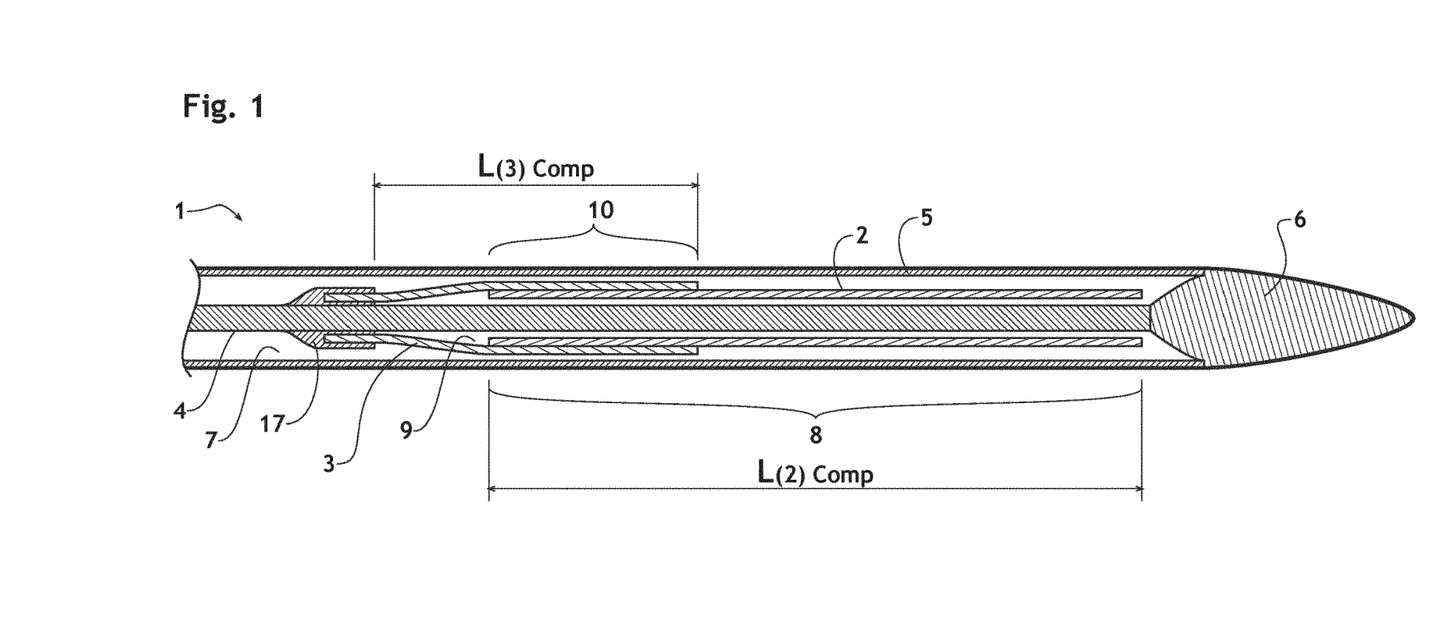
FIG. 1 is a cross-sectional side view of an embodiment of an intraluminal delivery apparatus according to the invention in a delivery configuration.

FIG. 1 shows an intraluminal stent delivery apparatus 1 according to an embodiment of the present invention in a delivery configuration. Only the distal end part of the apparatus is shown.

The intraluminal apparatus 1 comprises a stent receiving region 8 wherein a stent 2 has been introduced, a holding means 3 that maintains the stent 2 in place in the stent receiving region 8, a central inner shaft 4 and a retracting sheath 5. An atraumatic head 6 is disposed at the distal end of the sheath 5. The sheath 5 has a lumen 7 along its longitudinal axis and defines the stent receiving region 8 at the distal end of the lumen 7. The stent 2 is compressed up to its smaller diameter and pre-loaded within the stent receiving region 8 of the sheath's lumen 7 and disposed around the inner shaft 4. The holding means 3 defines a cavity 9. The proximal end of the holding means 3 constitutes the bottom of cavity 9 and is permanently joined to the inner shaft 4 with a joint 17. The holding means 3 is also compressed within the sheath 5 and the distal portion of the holding means 3 encircles the proximal portion of the stent 2 defining an overlapping region 10 of the holding means 3 and the stent 2 in compressed state. Details on the various components are provided below.

Figures 2, 2A:
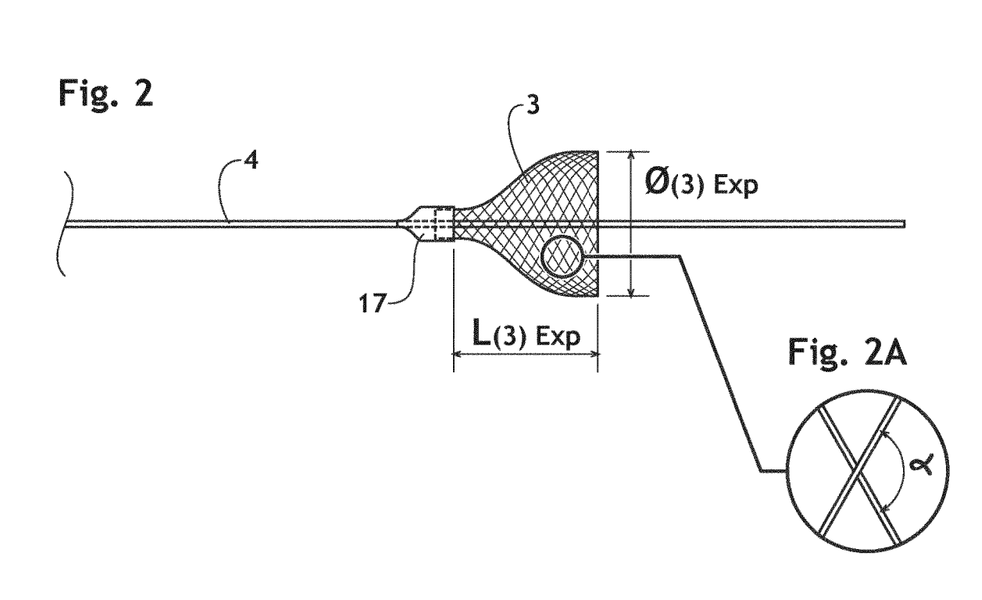
FIG. 2 is a side view of an embodiment of a holding means in expanded state with a distal portion of an inner shaft according to the invention.
FIG. 2A is a magnified view of a portion of the holding means illustrated in FIG. 2
Figure 3:
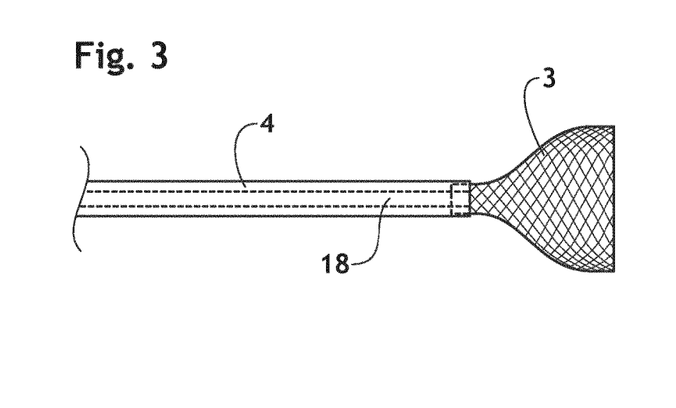
FIG. 3 is a side view of an embodiment of a holding means in expanded state according to the invention.

The inner shaft 4 may have a guide wire lumen 18 (see FIG. 3) so that the delivery intraluminal apparatus 1 may be advanced through the vessels of a body along a guide wire. The inner shaft 4 may extend along the inner side of the holding means 3, up to the atraumatic head 6 as shown in FIG. 1 or FIG. 2, or it may end at the proximal end of the holding means 3, as shown in FIG. 3. The inner shaft 4 can be made from a hypotube or from a solid wire.

The retracting sheath 5 can be made from any suitable bio-compatible material and lined with a low friction material like Teflon®. As implicated by FIG. 1, the sheath 5 exhibits sufficient structural integrity to compressively maintain the stent 2 and the holding means 3 in compressed state.

Figure 4:
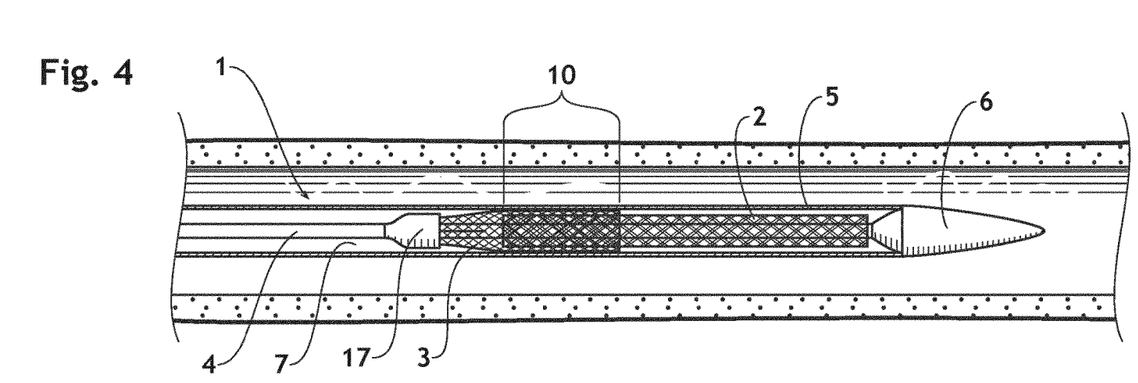
FIGS. 4 to 8 are simplified, cross-sectional views illustrating use of the intraluminal delivery apparatus of FIG. 1
Figure 5:
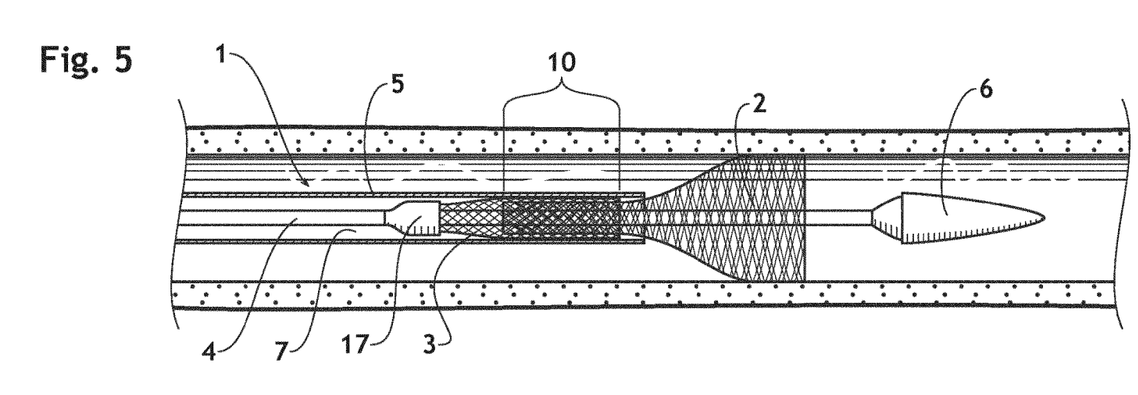

The stent 2 is configured to be self-expanding or have at least some self-expanding characteristics. As used herein the term "self-expanding" refers to the tendency of a device such as stent 2 to return to a predetermined diameter when unrestrained from an outer sheath such as retracting sheath 5, as depicted in FIGS. 4 to 8. In the present embodiment, when the stent 2 is disposed within the stent receiving region 8 of the lumen 7 of the retracting sheath 5, the stent 2 is maintained in its reduced diameter or pre-delivery configuration (i.e., compressed state) as shown in FIG. 4. At a desired location of a body lumen, the stent 2 is partially deployed by retracting sheath 5 toward the proximal end of the stent 2 as shown FIGS. 5-7. By releasing the stent 2 from the holding means 3 completely, the stent 2 will reach a deployed state in the body lumen as shown in FIG. 8.

The stent 2 preferably consists of or otherwise includes a meshed structure obtained by braiding or weaving filaments. In order to give the stent 2 good mechanical strength and good integrity over time, the meshed structure may be a multilayer braiding, as described in application U.S. Pat. No. 7,588,597. However, conventional monolayer braiding may be suitable.

The stent 2 can comprise metallic and non-metallic materials. Metallic materials include, without limitation, shape memory material such as Nitinol® and cobalt-based alloy (e.g., Elgiloy® and Phynox®), stainless seel, platinum, gold, titanium, tantalum, niobium, and combinations thereof and other biocompatible materials, as well as polymeric materials.

The holding means 3 has a self-expanding property and, preferably, consists of or otherwise includes a meshed structure obtained by braiding, weaving or knitting filaments. The material of the filaments is an elastic material and is advantageously chosen from shape memory material as mentioned above.

Figure 7:
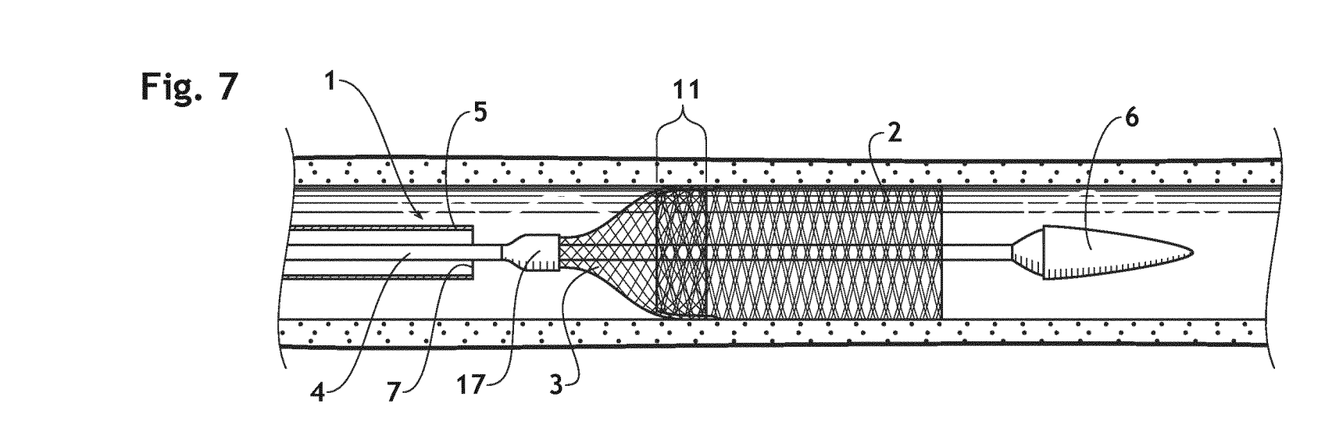
Figure 8:
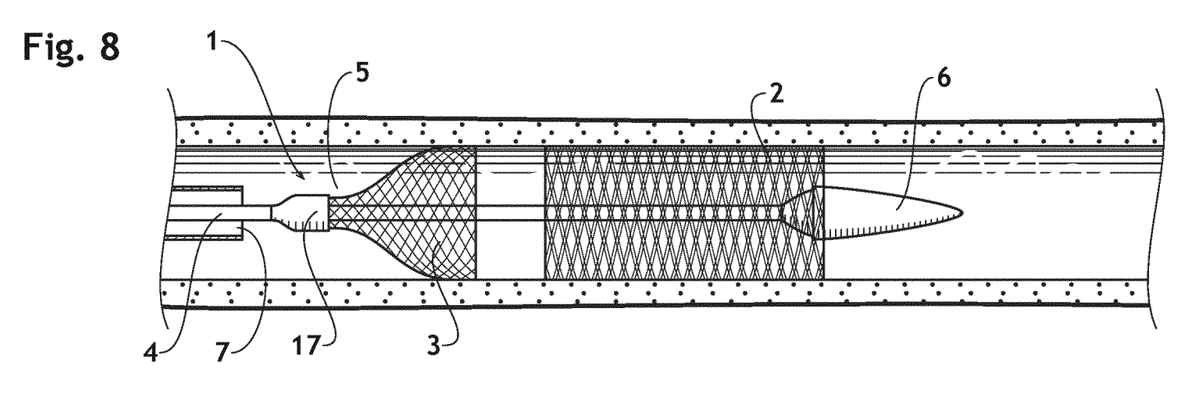
Figure 9:
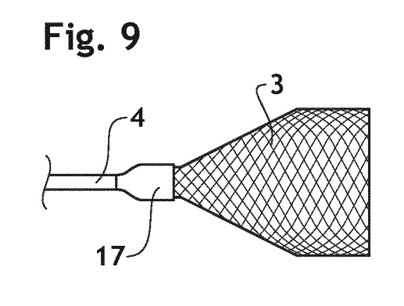
FIG. 9 is a side view of an embodiment of a holding means in expanded state with a distal portion of an inner shaft according to the invention.
Figure 10:
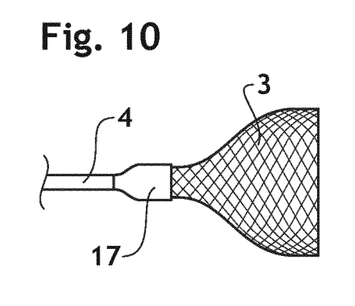
FIG. 10 is a side view of an embodiment of a holding means in expanded state with a distal portion of an inner shaft according to the invention.
Figure 11:
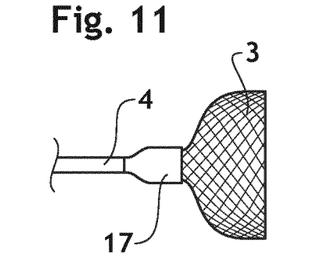
FIG. 11 is a side view of an embodiment of a holding means in expanded state with a distal portion of an inner shaft according to the invention.
Figure 12:
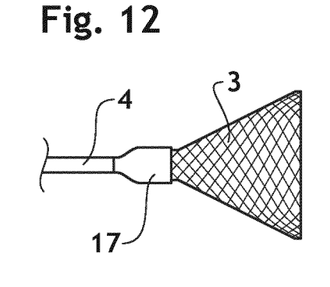
FIG. 12 is a side view of an embodiment of a holding means in expanded state with a distal portion of an inner shaft according to the invention.

The holding means 3 is configured to take a compressed shape having a relatively small and relatively uniform diameter when disposed within the retracting sheath 5 (i.e., "in compressed state") (see FIGS. 1 and 4) and to take a deployed shape having radially expanded diameter within the delivered location such as a body lumen (i.e., "in deployed state") (see FIGS. 7 and 8). As used herein the term of "expanded shape" or "expanded state" refers to respectively a "shape" or "state" exerted by a self-expanding property of a self-expanding object (e.g., stent 2 and holding means 3) when it is expanded without any obstacle to compress its structure (i.e., non-constricted state). Beside these two definitions, the term "nominal diameter", designates the diameter which is reached by the stent when placed in a vessel for which it has been designed.

The braided structure of the holding means 3 is able to provide an increased frictional force between the outer surface of the stent 2 and inner surface of the holding means 3 at the overlapping region 10 in their compressed state so as to make the holding means 3 grasp the stent 2 firmly enough to make the re-sheathing movement by drawing back the inner shaft 4 proximally. Surprisingly, as compared with other holding means comprised in devices the state of the art, the operator is thus able to force back the stent into its stent receiving region 8 up to an advanced stage of deployment so as to reposition the stent.

To deploy the stent 2 at a desired location in a body lumen, the distal end of the retracting sheath 5 is brought to the location (see FIG. 4) and the retracting sheath 5 is progressively withdrawn from over the stent 2 toward the proximal end of the intraluminal apparatus 1. Once the sheath 5 is adjacent the proximal end of the holding means 3 (see FIG. 5), the stent 2 is partially allowed to self-expand to a deployed shape.

Figure 6:
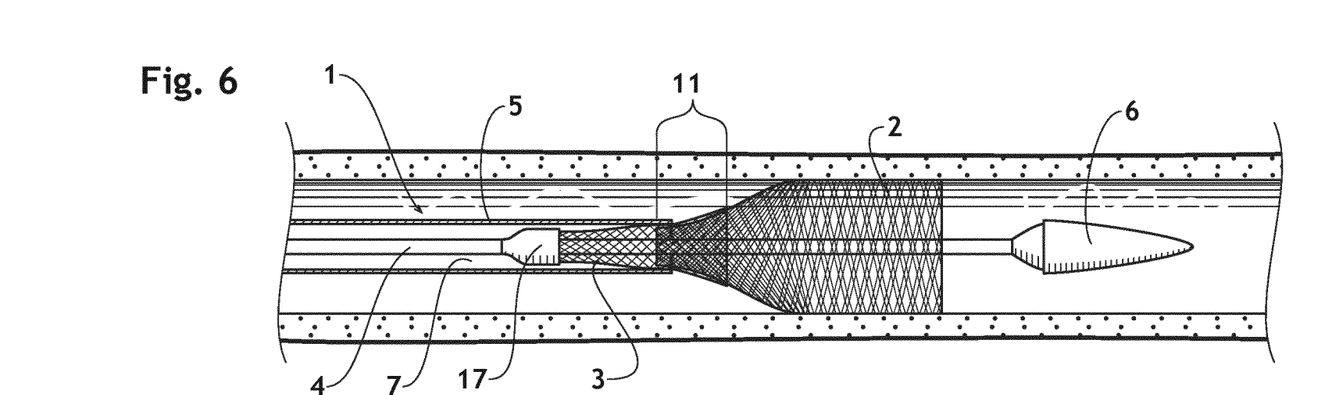

By continually retracting the sheath 5 proximally, the holding means 3 is released from the sheath 5 and deploys while shortening the overlapping region 11 between the stent 2 and the holding means 3 under the effect of the temperature of the organism and/or because of their inherent elasticity (FIGS. 6 and 7).

In order to prevent a stent's migration after implantation, an oversized stent is generally chosen which has a diameter in its "nominal" expanded state being 10-40% greater than the diameter of the body lumen at the implantation site. Such stent exerts a sufficient radial force on an inner wall of the body lumen and is thus fixed firmly where it is implanted.

Since, upon deployment, the radial force provided by the deployed part of the stent 2 onto the wall of a body lumen becomes greater than the grasping force of the deployed holding means 3 in its deployed state, the holding means 3 can release the stent 2 at the deployed position without displacing it longitudinally when retracting the inner shaft 4 proximally together with the sheath 5 (FIG. 8).

In some instances, a clinician may desire to only partially deploy the stent 2 and then evaluate before completely releasing the stent 2 from the intraluminal apparatus 1. For example, because of the considerable difference between the stent's length in its compressed state, $L_{(2)Comp}$, and in its deployed state, $L_{(2)Depl}$, the actual deployed position often differs from the position expected by the clinician. In order to increase the deployment accuracy, a function of re-sheathing the partially deployed stent 2 into the retracting sheath 5 is desired. If the clinician believes, under fluoroscopic guidance, that the stent 2 should be repositioned relative to the actual implantation site, the stent 2 can easily be re-sheathed by distally advancing the retracting sheath 5 until the stent 2 is disposed back within the stent receiving region 8 of the sheath 5. This re-sheathing movement is possible if the overlapping region 10 of the holding means 3 is still retained within the sheath 5 (see FIG. 5). Once the stent 2 is re-sheathed, the intraluminal apparatus 1 can be repositioned relative to the desired implantation site, and the process repeated until the clinician is satisfied with the achieved positioning. Alternatively, the re-sheathed stent 2 can be removed from the patient's vessel.

Although the holding means 3 in compressed state should hold the stent 2 sufficiently enough to ensure the re-sheathing movement, the holding means 3 in deployed state has to release the stent 2 at a desired implantation site without making undesired longitudinal migration of the stent 2.

In order to reduce the risk of the undesired stent's migration when releasing from the holding means 3 while ensuring the re-sheathing movement, in their expanded states the diameter of holding means 3 at its distal end, $\emptyset_{(3)exp}$, is preferably greater than the diameter of the stent 2, $\emptyset_{(2)exp}$. For example, when the stent's expanded diameter is less than 3 mm and used for a cerebral artery treatment, the holding means 3 should have greater diameter than the stent's diameter in their expended state, i.e., $\emptyset_{(3)exp} > \emptyset_{(2)exp}$, so as to minimize the undesired grasping force of the holding means 3 in its deployed state and to prevent the stent's migration when being completely released from the holding means 3.

In order to give the holding means 3 good mechanical strength and an adequate grasping force, the holding means 3 may consist of or otherwise comprise a multilayer braiding, as mentioned hereinabove. However, conventional monolayer braiding may also be suitable.

The cross section of the cavity 9 of the holding means 3 in its expanded state increases from the proximal end of the holding means 3, i.e., the bottom of the cavity 9, toward the distal end of the holding means 3, i.e., the top of the cavity 9. The shape of the holding means 3 may be selected from a group consisting of a bell-shape, a truncated cone-shape, and a truncated cone-shape with a cylindrical portion at its distal end as illustrated in FIGS. 9-12.

The difference between the length of the holding means 3 in its compressed state, $L_{(3)Comp}$, and the length in its expanded state, $L_{(3)Exp}$, is preferably as great as possible so that the overlapping region 11 of the holding means 3 and the stent 2 in their deployed state becomes shorter while keeping some overlapping region 10 in its compressed state within the intraluminal apparatus 1.

FIG. 2A shows angle α formed between two crossing braided filaments when the framework is expanded radially at body temperature without constraint (i.e., expanded state). The holding means 3 comprising a braided structure wherein angle α reaches at least 120°, preferably at least 150°, so that it can provide a high expansion ratio between the length in compressed state, $L_{(3)Comp}$, and the one in expanded state, $L_{(3)Exp}$. Namely, the difference in length between the compressed holding means, $L_{(3)Comp}$ (see FIG. 1) and the fully expanded holding means in the air without constraint, $L_{(3)}$ $_{Exp}$, (see FIG. 2) is proportionally great. Such an embodiment helps to solve the problem to reduce the risk of stent's migration when it is released from the holding means 3 at the desired implantation site, while ensuring the re-sheathing movement, namely repositioning function, during delivery.

The ratio of the length of the overlapping region 10, $L_{(10)comp}$, to the length of the stent 2, $L_{(2)comp}$, within the intraluminal apparatus 1 having the delivery configuration is at least 5% and at most 30%, preferably at least 10% and at most 25%, most preferably at least 15% and at most 25%, even more preferably at least 20% and at most 25%. If the ratio is under 5%, the grasping force of holding means 3 for re-sheathing movement is not sufficient and it will increase the risk of failure during re-sheathing movement. If the ratio is over 30%, the frictional force at the overlapping region 11 of the holding means and the stent 3 in their deployed state is too great to release the stent 2 safely from the holding means 3 without displacing the stent 2 longitudinally.

Figure 13:
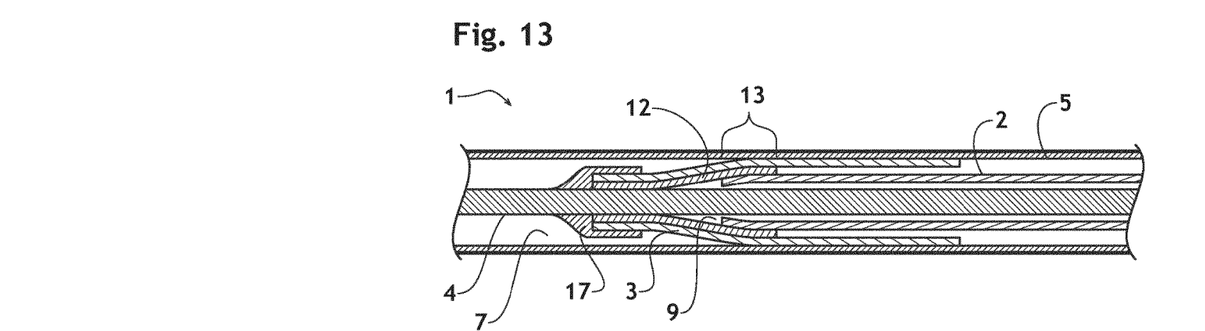
FIG. 13 is a side view of a middle portion of an intraluminal delivery apparatus in a delivery configuration as an embodiment of the invention.

As shown at FIG. 13, a low-frictional membrane 12 having a cylindrical or truncated cone shape can be disposed adjacent the bottom of inner cavity 9 of the holding means 3 and permanently joins the proximal end of the membrane 12 to the inner shaft 4 adjacent the bottom of the cavity 9. The distal portion of the membrane 12 is placed between the holding means 3 and the proximal end of the stent 2 so as to prevent the proximal end of the stent 2 from being stuck on a braided or woven body of the holding means 3. An overlapping region 13 of the membrane 12 with the stent 2 should be kept as small as possible. Preferably the overlapped length of membrane, $L_{(13)}$, is at most 20% of the length of the stent 2, $L_{(2)Comp}$, within intraluminal apparatus 1 having the delivery configuration so as to ensure a sufficient frictional force during the re-sheathing movement.

In another embodiment according to the present invention, the retracting sheath 5 and the holding means 3 may comprise a radiopaque material placed around the distal ends of the sheath 5 and the holding means 3 so as to provide a clinician with information about the positions of the holding means 3 relative to the position of the sheath 5 during deployment and to let the clinician know whether the intraluminal apparatus 1 is still capable to make the re-sheathing movement.

Figure 14:
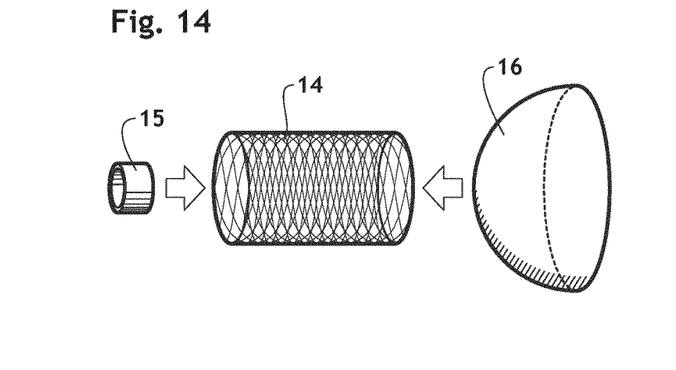
FIGS. 14 and 15 are simplified, perspective views illustrating steps of manufacturing a holding means according to the invention.
Figure 15:
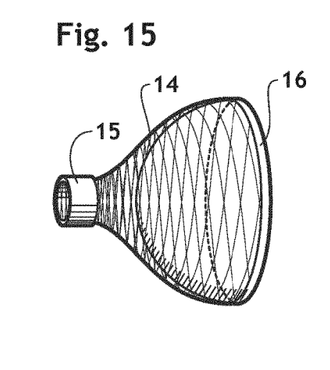

FIGS. 14 and 15 are schematic depictions of a first operation in the method of manufacturing a holding means 3 according to the invention. The holding means 3, before being shaped, may be in the form of a cylindrical tubular body 14 obtained by braiding filaments made of shape memory material.

The shaping step depicted in FIG. 14 begins by sliding an annulus 15, which acts as a diameter limiter, onto the proximal end of the tubular body 14. In order to increase the angle α, formed between the braided filaments, a bowl-shaped object 16 having a diameter larger than the one of the tubular body 14 may be inserted into the tubular body 14 from the distal end.

Once the appropriate shape has been achieved as shown in FIG. 15, in the case where the filaments are made of shape memory alloy, the holding means 3 undergoes a heat treatment that causes it to undergo a phase transition so as to make it memorize its expanded shape. In the case where the material used in a nickel/chrome/cobalt based alloy, the stent undergoes a high-temperature heat treatment to fix and stabilize the structure and eliminate the stresses in the metallographic structure.

Following this treatment, the holding means 3 is cooled and the annulus 15 and the bowl-shaped object 16 are discharged from the holding means 3.

The filaments of the end with reduced diameter (i.e., proximal end) are, then, gathered together to be joined to the inner shaft 4.

Figure 16:
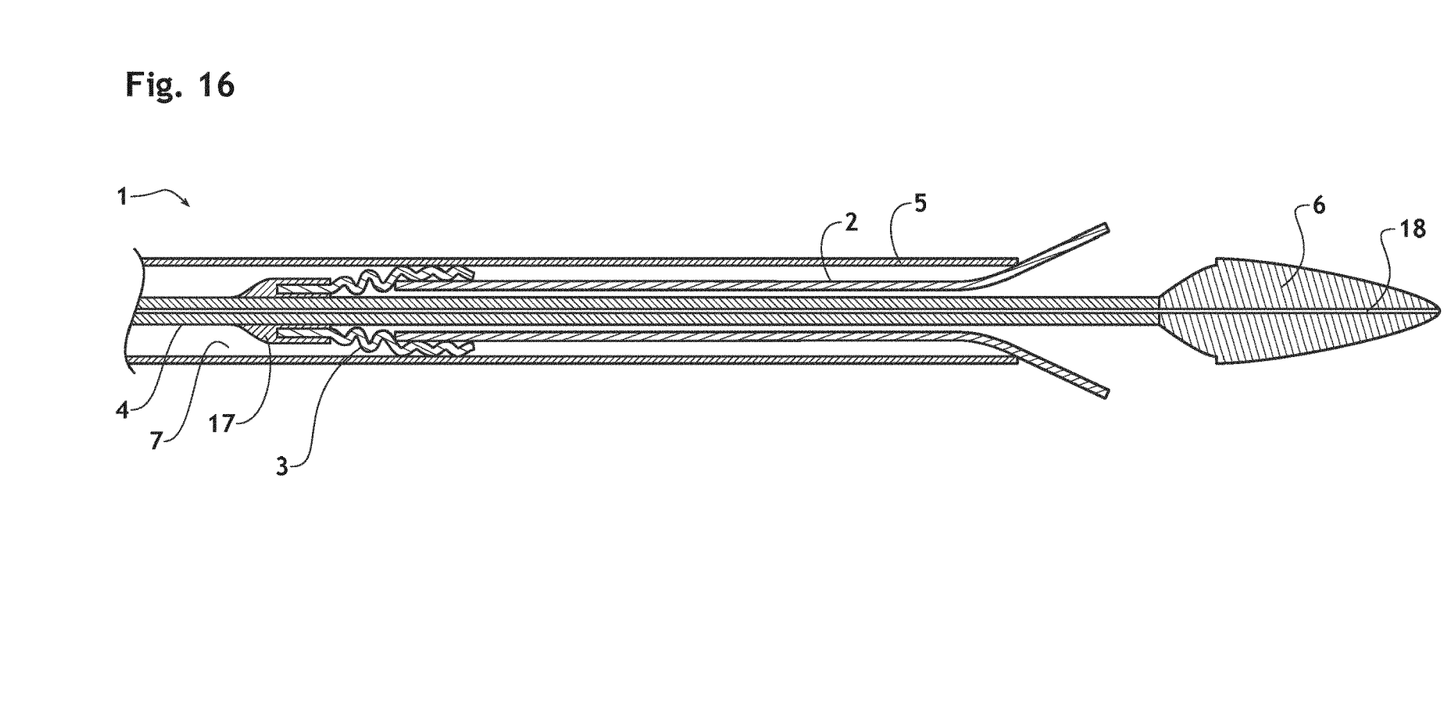
FIG. 16 is a cross-sectional side view of an embodiment of the stent delivery apparatus.
Figure 17:
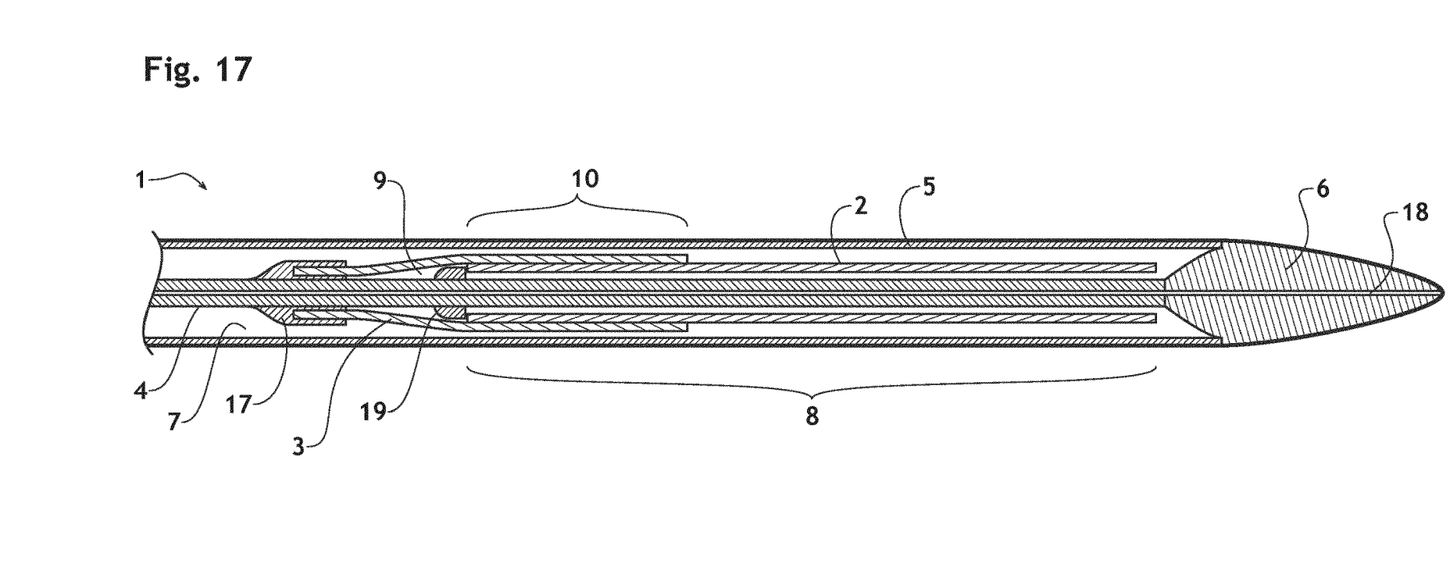
FIGS. 17 and 18 are cross-sectional side views of intraluminal delivery apparatuses in a delivery configuration according to the invention.

In order to obtain lower profile of the apparatus, thinner and more flexible holding means 3 are preferred. But this may cause reduction of push-ability thereof, because such thin structure s normally cannot provide sufficient rigidity and may crush around the distal end of the stent 2 by friction caused between the outer surface of the holding means 3 and the inner surface of the retracting sheath 5, as shown in FIG. 16. As a result, the stent cannot be delivered at a desired or rectified place. FIG. 17 shows the solution to this problem, which is a radial protrusion 19 surrounding one portion of the inner shaft 4. In the delivery configuration, the radial protrusion 19 being positioned outside and adjacent to the proximal end of the stent 2 in the inner cavity 9 of the holding means 3, i.e., abutting, so as to assist the inner shaft 4 in pushing the stent 2 toward the distal end of the apparatus 1. This allows to use of holding means 3 consisting of thinner and more flexible braided structure thus obtaining lower profile of the intraluminal apparatus 1 while keeping sufficient push-ability thereof.

Furthermore, in order to reduce undesired migration risk of the stent after its deployment in a vessel or a body lumen, the grasping force of holding means 3 has to be as low as possible when the holding means is completely uncovered by the retracting sheath 5, while it keeps sufficient push-ability and grasping ability inside of the retracting sheath. The present protrusion 19 can ensure a sufficient push-ability combined with a holding means 3 exhibiting a lower grasping force after its deployment, providing an increased deployment accuracy.

By adding the protrusion 19 onto the inner shaft 4, the overlap length of the holding means 3 with respect to the a stent 2 can be easily adjusted despite to the fact that stents of various length can be loaded by adapting the position of the protrusion 19 without modifying the basic structure of the holding means 3. It simplifies the manufacturing procedure and reduces production costs. The radial protrusion 19 is preferably a tubular shape made of metallic, polymeric or rubber. In order to assist the holding means 3 in pushing the stent more smoothly toward the distal end of the intraluminal apparatus while reducing the migration risk of the stent toward the proximal side, the outer diameter of the protrusion 19 is preferably at least 35% and at most 80% of the diameter of the lumen 7 of the retracting sheath 5, more preferably at least 50% and at most 70%, still more preferably at least 60%.

Figure 18:
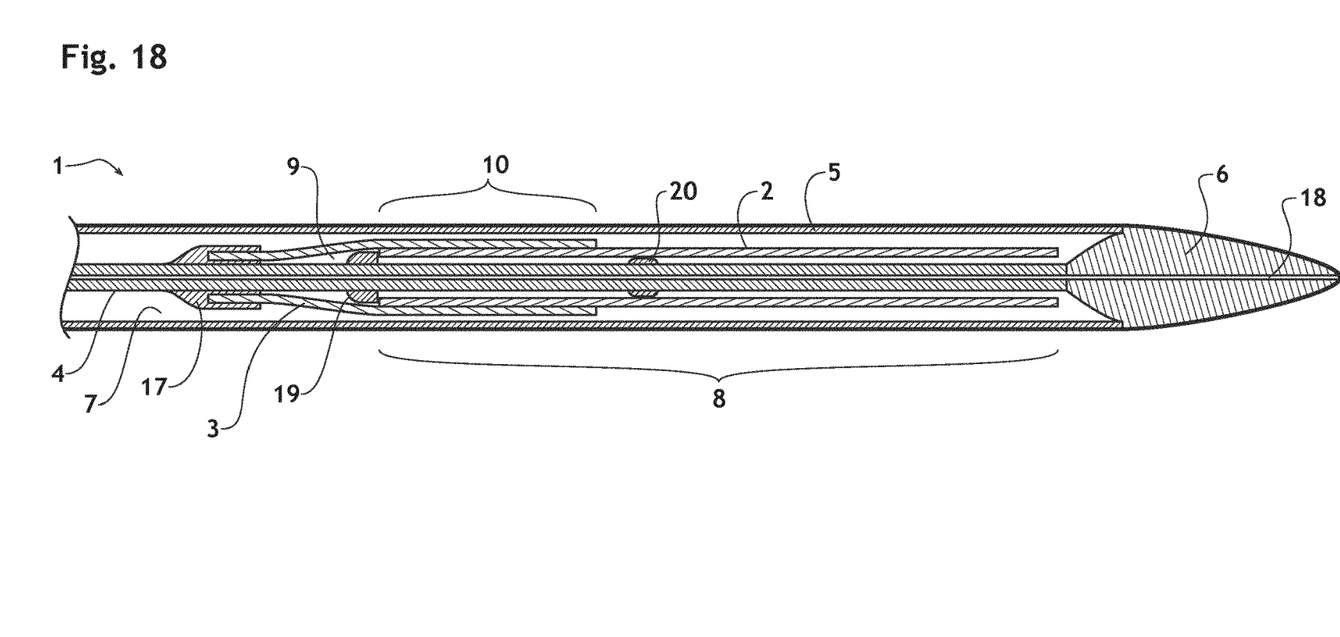
Figure 19:
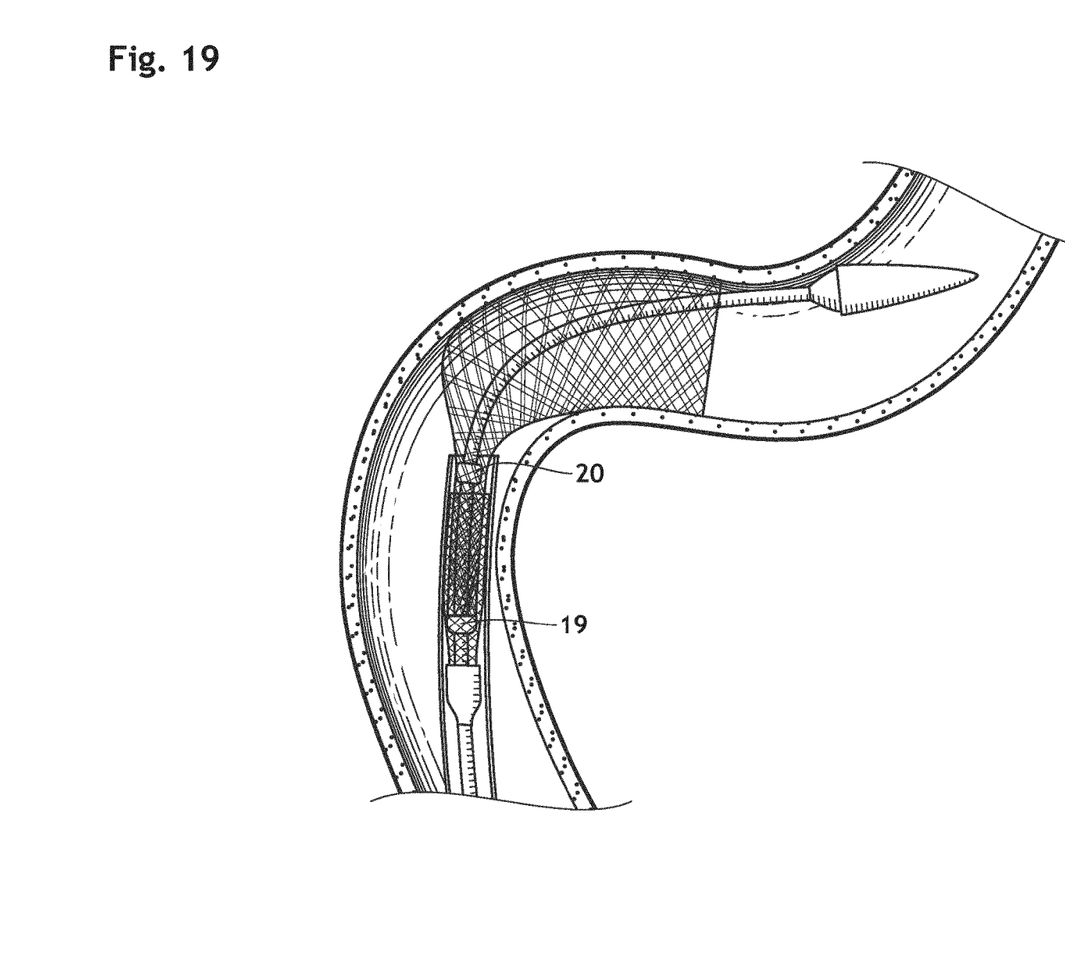
FIG. 19 is a simplified, cross-sectional view illustrating use of the intraluminal apparatus of FIG. 18

As shown in FIGS. 18 and 19, the inner shaft 4 may further comprise at least one supplemental protrusion 20 thereon, positioning inside of the stent 2 in the retracting sheath 5, so that the friction force exerted between the middle protrusion 20 and the inner surface of the sheath 5 assists the re-sheathing movement after the stent 2 is partially deployed. This feature proves particularly advantageous when the stent 2 is to be inserted e.g. in a curved vessel, as shown in FIG. 19.

The invention claimed is:
1. An intraluminal apparatus for delivering a self-expanding stent, the intraluminal apparatus extending along a longitudinal axis from a distal side to a proximal side, the intraluminal apparatus comprising, in a delivery configuration:
   a) a retracting sheath having a lumen along its longitudinal axis and slidably covering a stent receiving region at a distal end of the lumen;

b) an inner shaft longitudinally and centrally disposed in the intraluminal apparatus, at least a distal portion of the inner shaft being disposed within the retracting sheath;

c) the self-expanding stent in a compressed state disposed within the stent receiving region of the lumen; and a holding means delimitating an inner cavity, disposed adjacent to a proximal side of the stent in the retracting sheath, a proximal end of the holding means being permanently joined to the inner shaft;

wherein:

the holding means has a self-expanding property capable of radially expanding from a compressed state within the intraluminal apparatus to an expanded state;

the holding means includes a plurality of braided or weaved filaments made of an elastic material;

in the expanded state, a diameter of the inner cavity of the holding means is radially increased toward the distal end of the holding means;

when the intraluminal apparatus is in the delivery configuration, a distal portion of the holding means surrounding a proximal portion of the stent defines an overlapping region between the holding means and the stent;

a ratio $L_{(10)}/L_{(2)Comp}$ of a length of the overlapping region, $L_{(10)}$, to a length of the self-expanding stent in its compressed state, $L_{(2)Comp}$, being at least 10% and at most 30%.

2. The intraluminal apparatus according to claim 1, wherein the inner shaft further comprises a radial protrusion surrounding one portion of the inner shaft, this radial protrusion being positioned outside and adjacent to the proximal side of the stent in the inner cavity of the holding means.

3. The intraluminal apparatus according to claim 2, wherein an outer diameter of the radial protrusion is at least 35% and at most 80% of an inner diameter of the retracting sheath.

4. The intraluminal apparatus according to claim 2, wherein the inner shaft further comprises at least one supplemental protrusion disposed between the inner shaft and the stent distally from a distal end of the supplemental protrusion.

5. The intraluminal apparatus according to claim 2, wherein an outer diameter of the radial protrusion is at least 50% and at most 70% of an inner diameter of the retracting sheath.

6. The intraluminal apparatus according to claim 1, wherein, when expanded, the holding means adopts either one of:
(i) a U-shape;
(ii) a truncated cone-shape; or
(iii) a truncated cone-shape having a cylindrical portion at a distal end thereof.

7. The intraluminal apparatus according to claim 1, wherein the holding means is formed of a multilayer braiding.

8. The intraluminal apparatus according to claim 1, wherein the holding means is formed of braided filaments forming an angle (α) between them, the angle being at least 120° at least at a distal portion of the holding means when expanded.

9. The intraluminal apparatus according to claim 1, wherein, in their respective expanded state, the diameter of the holding means at its distal end, $\varnothing_{(3)Exp}$, is greater than a diameter of the stent, $\varnothing_{(2)Exp}$.

10. The intraluminal apparatus according to claim 1, wherein the elastic material of the filaments of the holding means is a shape memory material selected from a group consisting of a nickel-titanium alloy and a cobalt-based alloy.

11. The intraluminal apparatus according to claim 10, wherein the meshed structure is a multilayer braiding.

12. The intraluminal apparatus according to claim 1, wherein the self-expanding stent comprises a meshed structure of braided or weaved filaments.

13. The intraluminal apparatus according to claim 1, further comprising a membrane disposed within the inner cavity of the holding means, a proximal end of the membrane being permanently bounded to the inner shaft adjacent to a bottom of the inner cavity, a distal portion of the membrane being disposed around the proximal side of the stent.

14. The intraluminal apparatus according to claim 1, wherein the retracting sheath and the holding means comprise a radiopaque material around distal ends of the sheath and the holding means.

* * * * *